United States Patent
Dumenil

(10) Patent No.: US 8,152,867 B2
(45) Date of Patent: Apr. 10, 2012

(54) PROCESS, PLANT AND BIOFUEL FOR INTEGRATED BIOFUEL PRODUCTION

(75) Inventor: Jean-Charles Dumenil, Little Chalfont (GB)

(73) Assignee: BP Biofuels UK Ltd., Middlesex (GB)

( * ) Notice: Subject to any disclaimer, the term of this patent is extended or adjusted under 35 U.S.C. 154(b) by 615 days.

(21) Appl. No.: 12/336,719

(22) Filed: Dec. 17, 2008

(65) Prior Publication Data
US 2010/0146843 A1  Jun. 17, 2010

(51) Int. Cl.
*C10L 1/00* (2006.01)

(52) U.S. Cl. ....... 44/307; 435/160; 435/170; 435/289.1; 422/600; 568/840

(58) Field of Classification Search .................. 435/160, 435/289.1, 170; 568/840; 422/600
See application file for complete search history.

(56) References Cited

U.S. PATENT DOCUMENTS

| | | | |
|---|---|---|---|
| 4,612,286 A * | 9/1986 | Sherman et al. | 435/157 |
| 5,221,357 A * | 6/1993 | Brink | 127/43 |
| 7,098,009 B2 | 8/2006 | Shanmugam et al. | |
| 7,309,602 B2 | 12/2007 | David | |
| 2002/0069987 A1 | 6/2002 | Pye | |
| 2004/0231661 A1 | 11/2004 | Griffin et al. | |
| 2007/0099278 A1 * | 5/2007 | Aare | 435/134 |
| 2008/0033188 A1 | 2/2008 | Dumesic et al. | |
| 2008/0050800 A1 | 2/2008 | McKeeman et al. | |
| 2008/0057555 A1 * | 3/2008 | Nguyen | 435/165 |
| 2008/0138872 A1 * | 6/2008 | Smith et al. | 435/165 |
| 2008/0160593 A1 | 7/2008 | Oyler | |
| 2008/0227182 A1 | 9/2008 | Anderson et al. | |

FOREIGN PATENT DOCUMENTS

| | | |
|---|---|---|
| BR | 9706137 | 12/1997 |
| JP | 2009 183806 | 8/2009 |
| WO | WO 2007/095215 A2 | 8/2007 |
| WO | WO 2007/112090 A2 | 10/2007 |
| WO | WO 2008/045977 A2 | 4/2008 |
| WO | WO 2008/053284 A1 | 5/2008 |
| WO | WO 2008/060595 A2 | 5/2008 |
| WO | WO 2008/095033 A2 | 8/2008 |
| WO | WO 2008/151149 A2 | 12/2008 |
| WO | WO 2008/156651 A1 | 12/2008 |

OTHER PUBLICATIONS

E. Easterling et al. "The Effect of Glycerol as a Sole and Secondary Substrate on the Growth and Fatty Acid Composition of Rhodotorula Glutinis", Published Elsevier 2008, Bioresource Technology, pp. 356-361.
R. Marchal et al. "Large-Scale Enzymatic Hydrolysis of Agricultural Lignocellulosic Biomass. Part 2: Conversation into Acetone-Butanol", Bioresource Technologies, Jan. 24, 1992, pp. 205-217.

(Continued)

*Primary Examiner* — Cephia D Toomer
(74) *Attorney, Agent, or Firm* — John P. Poliak

(57) ABSTRACT

This invention relates to a process, a plant, and a biofuel for integrated biofuel production, such as with butanol, biodiesel, and/or sugar product. The integrated process includes the step of removing hexose from a feedstock to form a lignocellulosic material. The process also includes the step of converting the hexose to butanol and/or a biodiesel material, and the step of depolymerizing lignocellulosic material to form pentose and a residue. The process also includes the step of converting the pentose to butanol and/or a biodiesel material.

25 Claims, 5 Drawing Sheets

OTHER PUBLICATIONS

M. Mes-Hartree et al. "Butanol Production of Clostridium Acetobutylicum Grown on Sugars Found in Hemicellulose Hydrolysates", Biotechnology Letters vol. 4 (1982) pp. 247-252.

D. Savage et al. "Defossilling Fuel: How Synthetic Biology Can Transform Biofuel Production", ACS Chemical Biology vol. 3, Jan. 18, 2008, pp. 13-16.

I.C. Roberto et al. "Utilization of Sugar Cane Begasse Hemicellulosic Hydrolysate by *Pichia Stipitis* for the Production of Ethanol", Process Biochemistry, Aug. 14, 1990, pp. 15-21.

D. Chuan-Chao et al., "Biodiesel Generation From Oleaginous Yeast Rhodotorula Glutinis with Xylose Assimilating Capacity", African Journal, Sep. 19, 2007, pp. 2130-2134.

Y. Chin-Chung et al., "Enzymatic Saacharification and Fermentation of Xylose-Optimized Dilute Acid-Treated Lignocellulosics", Human Press Inc., vol. 121-124, 2005, pp. 947-961.

J. Fein et al. "Evaluation of D-Xylose Fermenting Yeasts for Utilization of Wood-Derived Hemocellulose Hydrolysate", Western Research Center, Feb. 7, 1984, pp. 682-690.

H. Jorgensen, et al., "Enzymatic Conversion of Lignocellulose into Fermentable Sugars: Challenges and Opportunities," Published online Jun. 27, 2007, Wiley InterScience (www.interscience.wiley.com); DOI: 10.1002/bbb.4; Biofuels, Bioprod. Bioref. 1:119-134 (2007).

S. Lemmel et al. "Fermentation of Xylan by Clostridium Acetobutylicum", Enzyme Microb Technol, Oct. 3, 1985, pp. 217-221.

N. Qureshi et al., Butanol, 'a superior biofuel' Production From Agricultural Residues (renewable biomass): Recent progress in Technology¶ Biofpr, Mar. 3, 2008, pp. 319-330.

D.R. Woods, "The Genetic Engineering of Microbial Solvent Production", Elsevier Science Ltd., Jul. 1995 pp. 259-264.

B. Yang et al. "Pretreatment: the Key to Unlocking Low-Cost Cellulosic Ethanol," Published online Dec. 17, 2007 in Wiley InterScience (www.interscience.wiley.com); DOI: 10.1002/bbb.49, Biofuels, Bioprod. Bioref. 2:26-40 (2008).

\* cited by examiner

PROCESS, PLANT AND BIOFUEL FOR INTEGRATED BIOFUEL PRODUCTION

BACKGROUND

1. Technical Field

This invention relates to a process, a plant, and a biofuel for integrated biofuel production, such as with butanol, biodiesel, and/or sugar product.

2. Discussion of Related Art

Tightening oil supply and escalating energy prices along with environmental concerns over nonrenewable resources have prompted significant interest and research into alternative fuels. Efforts to reduce carbon emissions and greenhouse gases are also driving investment into alternative fuels.

Anderson et al., U.S. Patent Application Publication 2008/0227182 discloses systems and methods for enzymatic hydrolysis of lignocellulosic materials. The enzymatic hydrolysis converts hexose sugars from cellulose and pentose sugars from hemicellulose. The system produces a mixed stream of 6-carbon sugars and 5-carbon sugars and then seeks to ferment them to ethanol with a microorganism capable of fermenting both glucose and xylose to ethanol. Anderson et al. does not disclose segregated 6-carbon sugar and 5-carbon sugar processes.

McKeeman et al., U.S. Patent Application Publication 2008/0050800, discloses a method and apparatus for a multi-system bioenergy facility. The multi-system bioenergy facility generates electricity with biogas from an anaerobic digester and ethanol from an ethanol production facility. The multi-system bioenergy facility also generates triglycerides with algae from bioreactors supplied with nutrient rich waste water from the anaerobic digester and carbon dioxide rich flue gas from a steam production facility. McKeeman et al. does not disclose a sugar to biodiesel method or apparatus.

Aare, U.S. Patent Application Publication 2007/0099278, discloses production of biodiesel from a combination of corn (maize) and other feed stocks. The process separates corn oil and corn starch which is enzymatically converted to fermentable sugars with a liquification and saccharification process. Yeast is added to ferment the sugars before distillation to produce ethanol. The corn oil is fed into a transesterification vessel where ethanol with catalyst forms crude biodiesel and crude glycerin. The amount of biodiesel is limited to the small amount of oil in the corn. Aare does not disclose a sugar to biodiesel process.

However, even with the above improvements in the processes, there is a need and a desire to coproduce biodiesel with butanol and/or sugar product in a manner that is less expensive and more integrated than known processes. There is also a need and a desire to maintain separated biological pathways for hexose conversion and pentose conversion.

SUMMARY

This invention relates to a process and a plant for integrated biofuel production, such as with butanol, biodiesel, and/or sugar product. In a broad embodiment, this invention includes production of butanol and/or biodiesel from hexose beneficially integrated with separate production of butanol and/or biodiesel from pentose.

The invention also includes using inexpensive lignocellulosic waste material to coproduce biofuel. The lignocellulosic material provides a source of extractable pentose from the hemicellulose. The pentose provides the building components to produce biofuel, such as by a biological pathway. The balance or residue after pentose extraction can be treated to extract additional hexose from the cellulose or can be burned to produce energy or power.

Desirably, the process separates or segregates the hexose and pentose streams to avoid mixed feeds to biological pathways or processes that preferentially consume hexose. Also desirably, the pentose removal process does not break down or liberate hexose from the cellulose, according to one embodiment.

According to a first embodiment, the invention includes an integrated process of coproducing butanol and biodiesel. The process includes the step of removing hexose from a feedstock to form a lignocellulosic material. The process also includes the step of converting the hexose to butanol, and the step of depolymerizing the lignocellulosic material to form pentose and a residue. The process also includes the step of converting the pentose to a biodiesel material.

According to a second embodiment, the invention includes an integrated process of coproducing butanol and biodiesel. The process includes the step of removing hexose from sugarcane to form a lignocellulosic material, and the step of converting the hexose to butanol. The process also includes the step of depolymerizing the lignocellulosic material to form pentose and a residue, and the step of converting the pentose to a biodiesel material. The process also includes the step of consuming the residue to produce energy, and the step of reacting the biodiesel material with methanol or another alcohol to form a biodiesel product and glycerin. The process also includes the step of converting the glycerin to additional biodiesel material. The process produces a mass ratio of biodiesel to butanol of at least about 0.2 kilotons of biodiesel to 1.0 kiloton of butanol.

According to a third embodiment, the invention includes an integrated butanol and biodiesel plant. The plant includes a hexose removal unit adapted for removing hexose from a feedstock to form a lignocellulosic material, and a hexose conversion unit adapted for converting hexose to butanol. The plant also includes a pentose depolymerization unit adapted for removing pentose from the lignocellulosic material to form a residue. The plant also includes a pentose conversion unit adapted for converting pentose to a biodiesel material, and an energy conversion unit adapted for consuming the residue and producing energy.

According to a fourth embodiment, the invention includes an integrated process of coproducing biofuels. The process includes the step of removing hexose from a feedstock to form a lignocellulosic material, and the step of converting the hexose to butanol and/or a biodiesel material. The process also includes the step of depolymerizing the lignocellulosic material to form pentose and a residue, and the step of converting the pentose to butanol and/or a biodiesel material.

According to a fifth embodiment, the invention includes a biofuel made by any of the plants or processes described herein, such as butanol, biogasoline, biodiesel, and/or the like.

BRIEF DESCRIPTION OF THE DRAWINGS

The accompanying drawings, which are incorporated in and constitute a part of this specification, illustrate embodiments of the invention and, together with the description, serve to explain the features, advantages, and principles of the invention. In the drawings.

DETAILED DESCRIPTION

This invention may include a process and a plant for integrated biofuel production, such as with butanol, biodiesel, and/or sugar product. According to one embodiment, the invention may include a sugar to diesel pathway integrated or combined with a route to ethanol, purified sugar, rum, molasses, and/or the like. The term "sugar to diesel" broadly refers to pathways from a carbohydrate feedstock into hydrocarbons or oxygenated hydrocarbons useable either directly or after product upgrading as diesel fuel and/or aviation fuel components. Suitable biodiesel materials may include triglycerides, fatty acids, alkanes, alkenes, pure hydrocarbons, and/or the like.

Introduction of the sugar to diesel pathway within the biofuels route enables the use of both pentose and hexose ($C_5$ and $C_6$ sugars respectively). The invention also may include the integration of an upgrade phase in the process, such as esterification of triglycerides or fatty acids with the use of an alcohol. Alcohols for esterification may include methanol, ethanol, propanol, butanol, hexanol, and/or the like. The alcohol for esterification may be made on site or coproduced, such as from a biological source. In the alternative, the alcohol for esterification may be brought in, such as from a third party supplier. The byproduct or output glycerin from the esterification process may be injected back into the sugar to diesel pathway, such as food for organisms resulting in conversion to a fatty acid.

This invention may cover the integration of a "sugar to diesel"* pathway with a route to ethanol, butanol, and/or any other component suitable for fuel applications. According to one embodiment, the introduction of the sugar to diesel pathway can enable the use of a pentose sugar source ($C_5$) to a useful fuel product.

Figure 1:
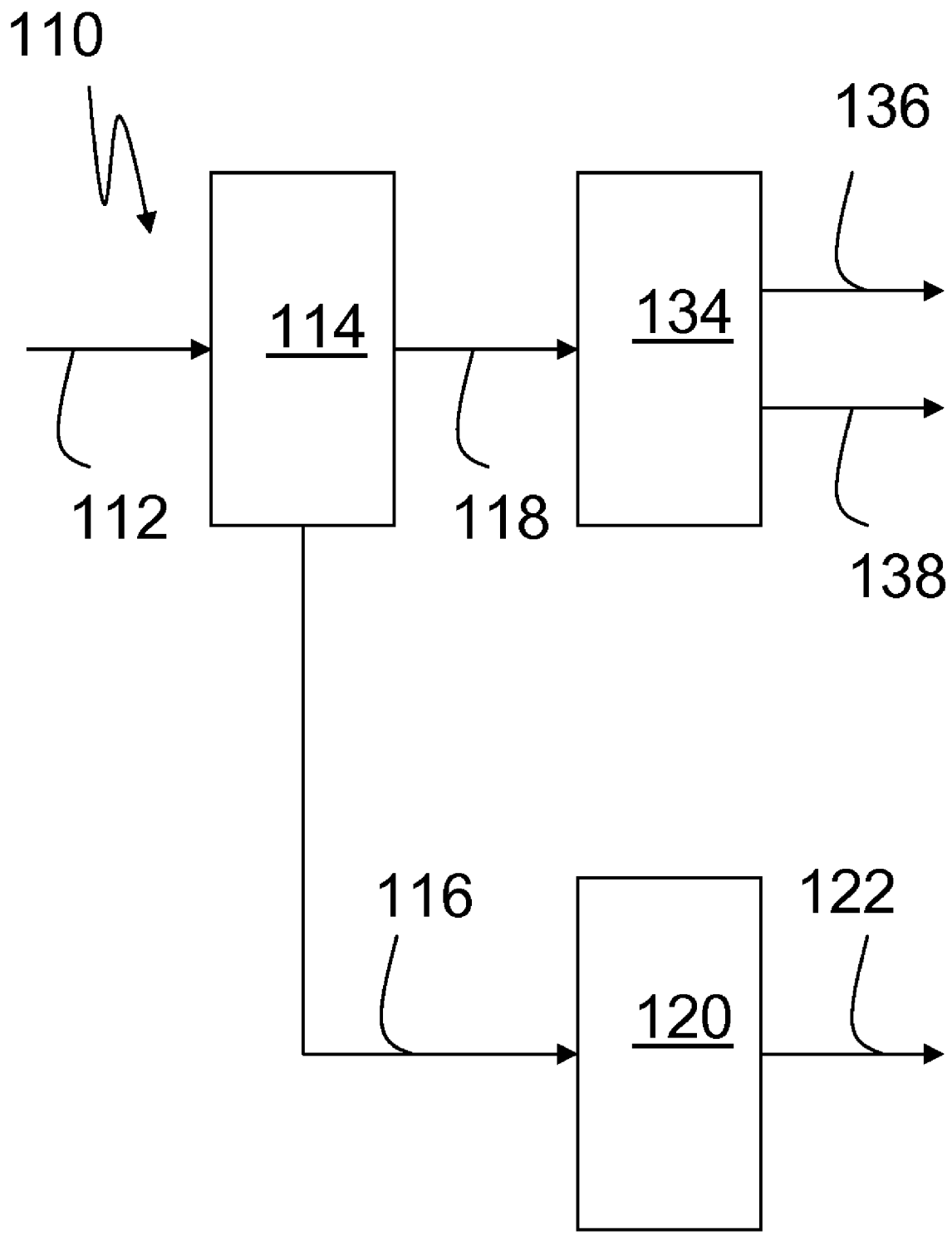
FIG. 1 illustrates a conventional alcohol plant.

FIG. 1 shows a conventional ethanol plant 110 having a feedstock line 112 connected to a hexose removal unit 114, such as a crushing unit. The hexose removal unit 114 connects to a hexose line 116 and a lignocellulosic material line 118. The hexose line 116 connects to a hexose conversion unit 120, such as a conventional fermentor. The hexose conversion unit 120 produces alcohol by an alcohol line 122. The lignocellulosic material line 118 connects to a powerhouse 134, such as for producing energy. Energy may be supplied from the powerhouse 134 by a steam line 136 and/or an electricity line 138.

Figure 2:
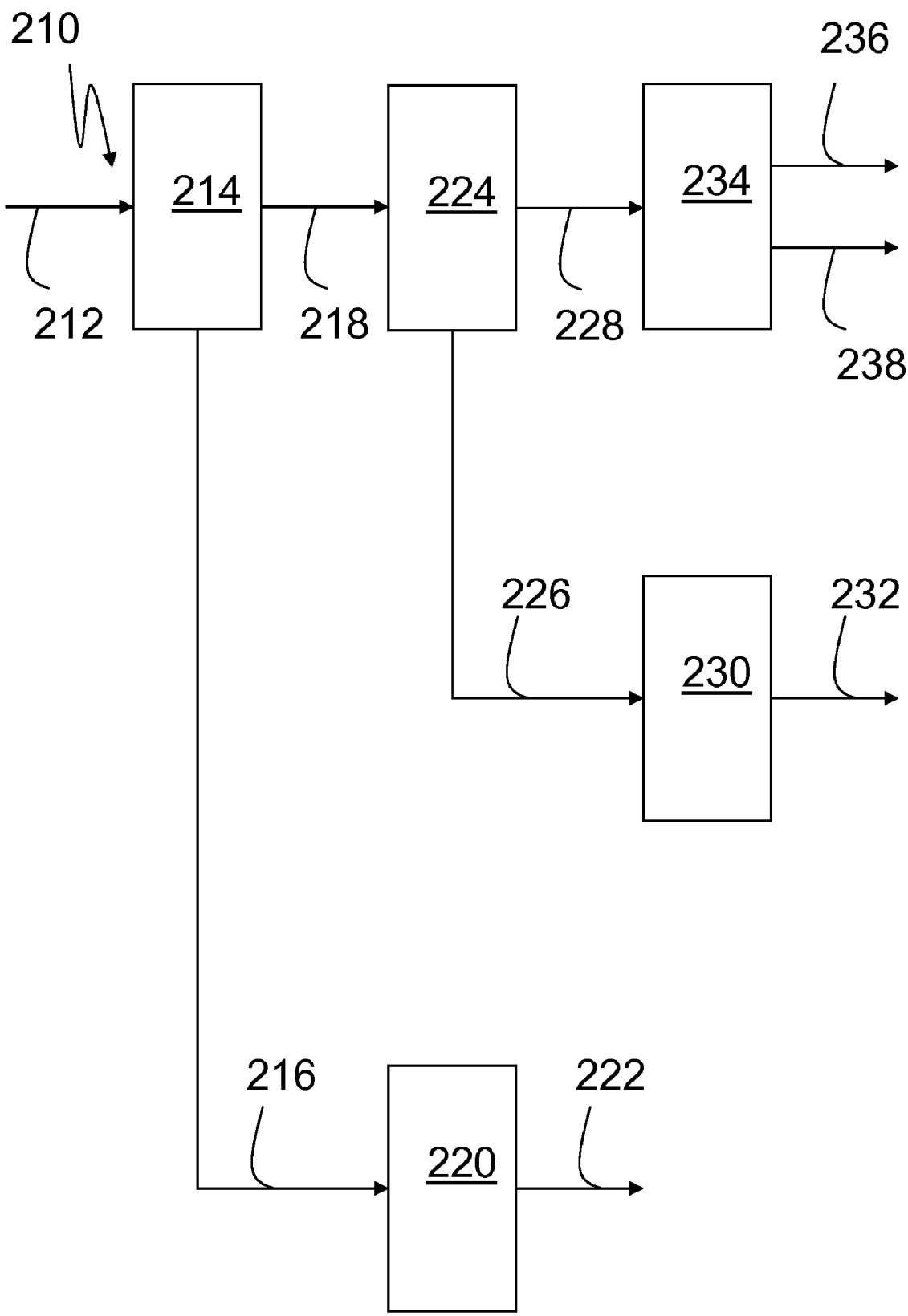
FIG. 2 illustrates an integrated biofuels plant, according to one embodiment.

FIG. 2 shows an integrated biofuels plant 210, according to one embodiment. The integrated plant 210 includes a feedstock line 212 connected to a hexose removal unit 214. The hexose removal unit 214 connects to a hexose line 216 and a lignocellulosic material line 218. The hexose line 216 connects to a hexose conversion unit 220. The hexose conversion unit 220 produces butanol by a butanol line 222. The same or additional hexose fermentors may be used for producing different butanol isomers or streams. The lignocellulosic material line 218 connects to a pentose depolymerization unit 224 connected to a pentose line 226 and a residue line 228. The pentose line 226 connects to a pentose conversion unit 230 with a biodiesel material line 232. Optionally, the residue line 228 connects to a powerhouse 234 with a steam line 236 and/or an electricity line 238. In the alternative, the hexose conversion unit 220 may produce biodiesel with a biodiesel material line (not shown). Also in the alternative, the pentose conversion unit 230 may produce butanol with a butanol line (not shown).

Figure 3:
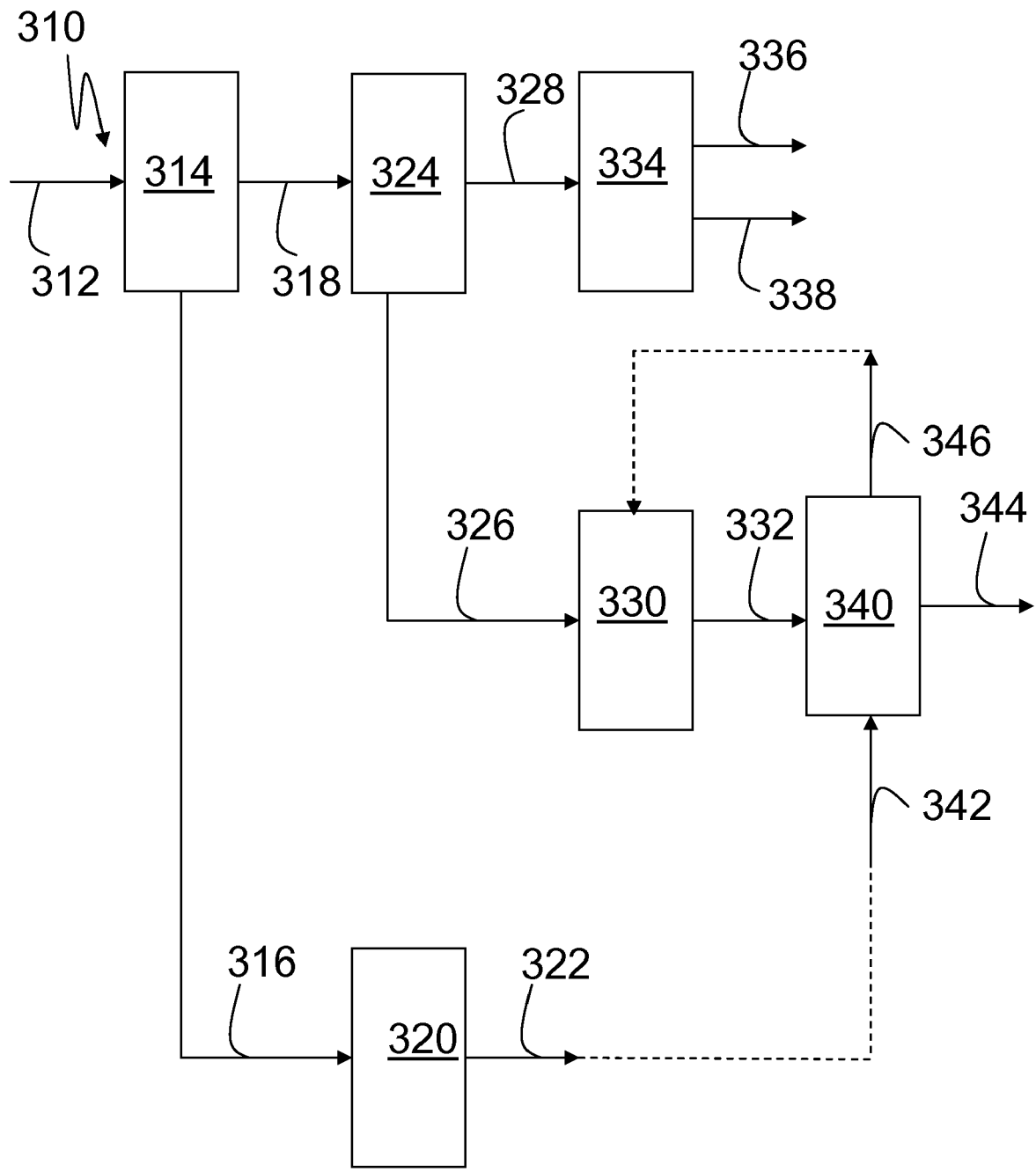
FIG. 3 illustrates an integrated biofuels plant with an esterification unit, according to one embodiment.

FIG. 3 shows an integrated biofuels plant 310 with an esterification unit 340, according to one embodiment. The integrated plant 310 includes a feedstock line 312 connected to a hexose removal unit 314. The hexose removal unit 314 connects to a hexose line 316 and a lignocellulosic material line 318. The hexose line 316 connects to a hexose conversion unit 320. The hexose conversion unit 320 produces butanol by a butanol line 322. The lignocellulosic material line 318 connects to a pentose depolymerization unit 324 with a pentose line 326 and a residue line 328. The pentose line 326 connects to a pentose conversion unit 330 with a biodiesel material line 332. Optionally, the residue line 328 connects to a powerhouse 334 with a steam line 336 and/or an electricity line 338. The biodiesel material line 332 connects to an esterification unit 340 supplied by an alcohol-based material line 342. Optionally and as shown as a dashed line, the alcohol-based material line 342 connects to the butanol line 322, such as for additional integration. The esterification unit 340 has a biodiesel product line 344 and a glycerin line 346. Optionally and as shown as a dashed line, the glycerin line 346 connects to the pentose conversion unit 330, such as to recycle and produce additional biodiesel material.

Figure 4:
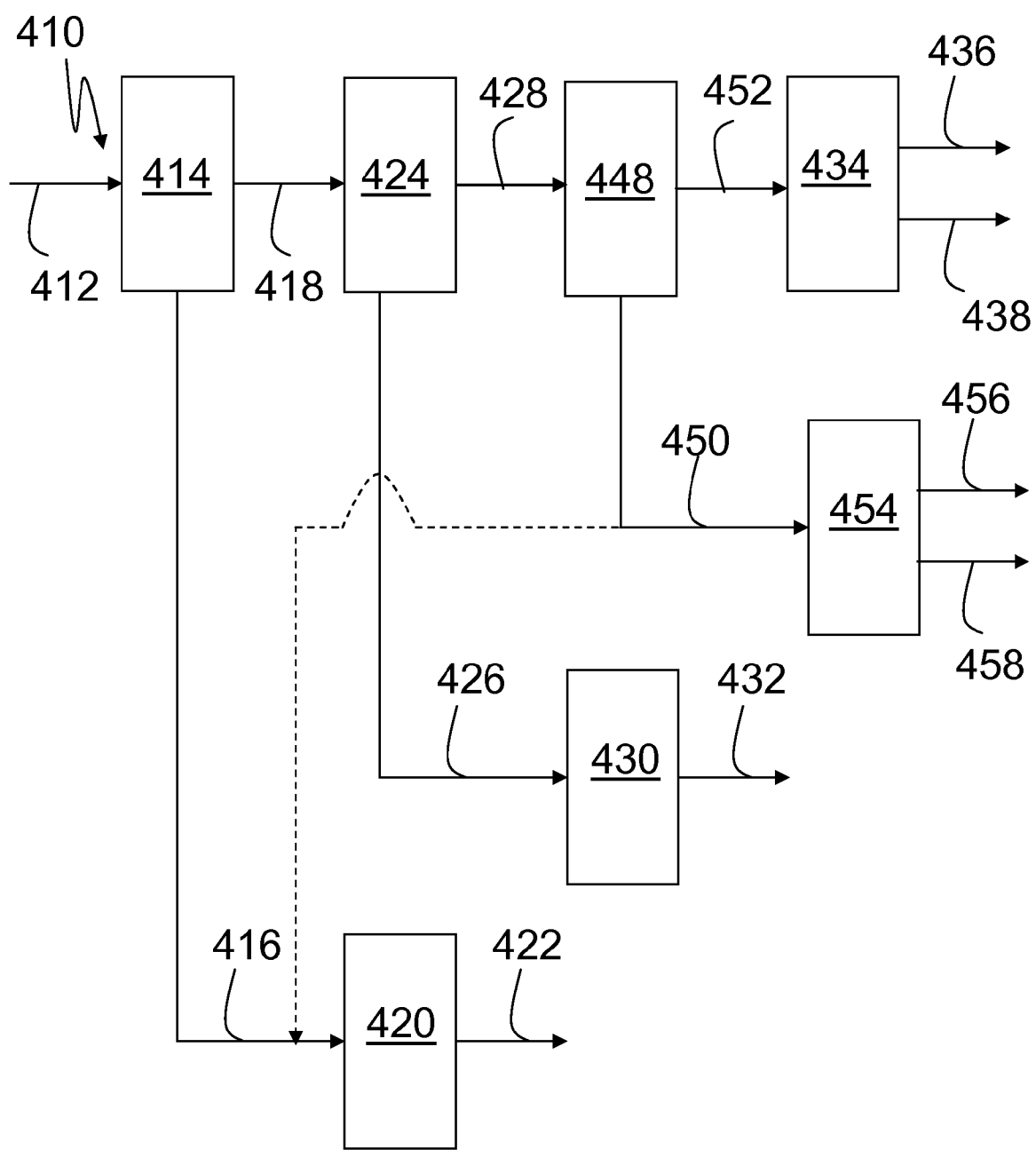
FIG. 4 illustrates an integrated biofuels plant with a hexose depolymerization unit, according to one embodiment.

FIG. 4 shows an integrated biofuels plant 410 with a hexose depolymerization unit 448, according to one embodiment. The integrated plant 410 includes a feedstock line 412 connected to a hexose removal unit 414. The hexose removal unit 414 connects to a hexose line 416 and a lignocellulosic material line 418. The hexose line 416 connects to a hexose conversion unit 420. The hexose conversion unit 420 produces butanol by a butanol line 422. The lignocellulosic material line 418 connects to a pentose depolymerization unit 424 with a pentose line 426 and a residue line 428. The pentose line 426 connects to a pentose conversion unit 430 with a biodiesel material line 432. The residue line 428 connects to a hexose depolymerization unit 448 with a second hexose line 450 and a reduced residue line 452. Optionally and a shown in a dashed line, the second hexose line 450 may connect with the hexose line 416, such as for consumption in the hexose conversion unit 420 to butanol. In the alternative, the second hexose line 450 may connect with a second hexose conversion unit 454 with a second butanol line 456 and/or a second biodiesel material line 458. Optionally, the reduced residue line 452 connects to a powerhouse 434 with a steam line 436 and/or an electricity line 438.

Figure 5:
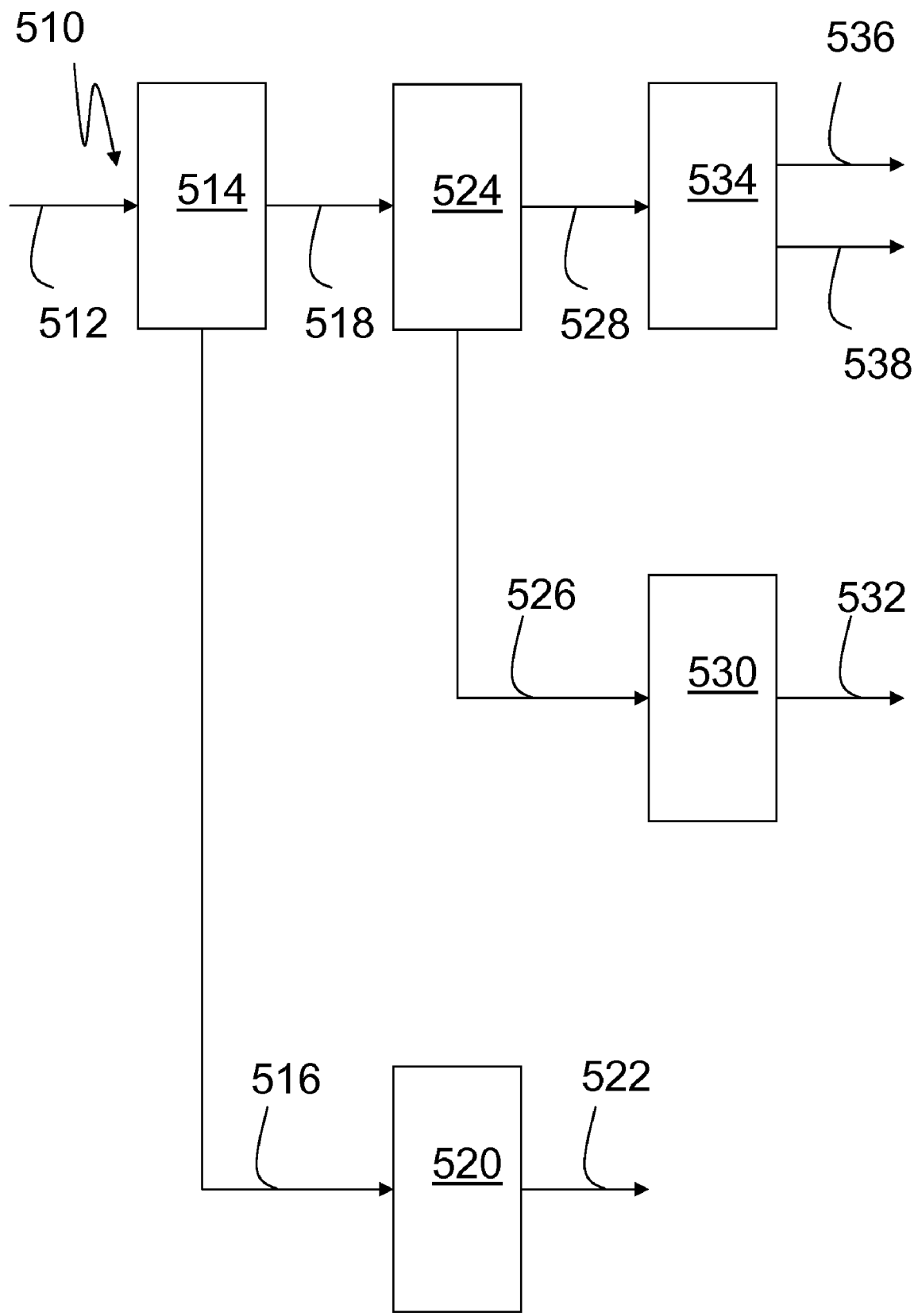
FIG. 5 illustrates an integrated sugar product and biofuel plant, according to one embodiment.

FIG. 5 shows an integrated sugar product and biofuel plant 510, according to one embodiment. The integrated plant 510 includes a feedstock line 512 connected to a hexose removal unit 514. The hexose removal unit 514 connects to a hexose line 516 and a lignocellulosic material line 518. The hexose line 516 connects to a hexose conversion unit 520. The sugar product unit 520 produces sugar product by a sugar product line 522. The lignocellulosic material line 518 connects to a pentose depolymerization unit 524 with a pentose line 526 and a residue line 528. The pentose line 526 connects to a pentose conversion unit 530 with a butanol line (not shown) and/or biodiesel material line 532. Optionally, the residue line 528 connects to a powerhouse 534 with a steam line 536 and/or an electricity line 538.

According to one embodiment, the invention may include an integrated process of coproducing butanol and biodiesel. The process may include the step of removing hexose from a feedstock to form a lignocellulosic material and the step of converting the hexose to butanol. The process may also include the step of depolymerizing the lignocellulosic material to form pentose and a residue, and the step of converting the pentose to a biodiesel material.

Biofuel broadly refers to components or streams suitable for use as a fuel or a combustion source derived from renewable sources, such as may be sustainably be produced and/or have reduced or no net carbon emissions to the atmosphere. Renewable resources may exclude materials mined or drilled, such as from the underground. Desirably, renewable resources may include single cell organisms, microorganisms, multicell organisms, plants, fungi, bacteria, algae, cultivated crops, non-cultivated crops, and/or the like.

Biogasoline broadly refers to components or streams suitable for blending into the gasoline or octane pool or supply derived from renewable sources, such as methane, hydrogen, syn (synthesis) gas, methanol, ethanol, propanol, butanol (all isomers), dimethyl ether, methyl tert-buyl ether, ethyl tert-butyl ether, hexanol, aliphatic compounds (straight, branched, and/or cyclic), heptane, isooctane, cyclopentane, aromatic compounds, ethyl benzene, and/or the like. Butanol broadly refers to products and derivatives of 1-butanol, 2-butanol, iso-butanol, other isomers, and/or the like. Biogasoline may be used in spark ignition engines, such as automobile gasoline internal combustion engines. According to one embodiment, the biogasoline and/or biogasoline blends meet or comply with industrially accepted fuel standards.

Desirably, biogasoline may be used by itself and/or blended with other fuels, such as mineral oil based hydrocarbons or refinery produced products. Biogasoline blends may include any suitable amount by volume of biogasoline, such as at least about 5 percent, at least about 10 percent, at least about 15 percent, at least about 20 percent, at least about 30 percent, at least about 40 percent, at least about 50 percent, at least about 60 percent, at least about 70 percent, at least about 80 percent, at least about 85 percent, at least about 90 percent, at least about 95 percent, about 100 percent, and/or the like.

Biodiesel broadly refers to components or streams suitable for blending into the diesel or cetane pool or supply derived from renewable sources, such as fatty acid esters, triglycerides, lipids, fatty alcohols, alkanes, naphthas, distillate range materials, paraffinic materials, aromatic materials, aliphatic compounds (straight, branched, and/or cyclic), and/or the like. Biodiesel may also refer to aviation fuels Get), lubricant base stocks, kerosene fuels, and/or the like. Biodiesel may be used in compression engines, such as automotive diesel internal combustion engines. In the alternative, the biodiesel may also be used in gas turbines, heaters, and/or the like. According to one embodiment, the biodiesel and/or biodiesel blends meet or comply with industrially accepted fuel standards.

Desirably, biodiesel may be used by itself and/or blended with other fuels, such as mineral oil based hydrocarbons or refinery produced products. Biodiesel blends may include any suitable amount by volume of biodiesel, such as at least about 2 percent, at least about 5 percent, at least about 10 percent, at least about 15 percent, at least about 20 percent, at least about 30 percent, at least about 40 percent, at least about 50 percent, at least about 60 percent, at least about 70 percent, at least about 80 percent, at least about 85 percent, at least about 90 percent, at least about 95 percent, about 100 percent, and/or the like.

Coproducing broadly refers to making or manufacturing at the same time and/or substantially the same time, such as a substantial amount of product A and product B. Integrated broadly refers to synergistic benefits from combining two or more items, devices, steps, and/or processes.

Feedstock broadly refers to any suitable carbohydrate containing material, such as sugar cane, energy cane, corn, maize, sorghum, sweet sorghum, sugar beet, rice, cassava, and/or the like. Energy cane broadly refers to grasses that have less soluble sugar than sugar cane and an increased fiber content. Feedstocks may include food materials for human or cattle consumption. In the alternative, feedstocks may exclude food materials for human or cattle consumption, such as switchgrass. Feedstocks desirably may include plant matter, algae, invertebrate animals, vertebrate animals and/or the like.

Carbohydrates broadly refer to compounds having the general formula $C_xH_{2x}O_x$ where x includes any suitable integer, such as 1, 2, 3, 4, 5, 6, 7, 8, 9, 10, 20, 50, and/or the like. Other chemical formulas for carbohydrates and/or sugars are within the scope of the invention. Sugars broadly refer to carbohydrate compounds having a generally at least somewhat sweet sensation on the tongue. Sugars may be building blocks or components of more complex molecules, such as starches, hemicellulose, cellulose, and/or the like.

According to one embodiment, feedstocks may include soybeans, rapeseed, jatropha, and/or the like. In the alternative, feedstocks may exclude relatively high oil bearing or oil containing materials.

Hexose broadly refers to six (6) carbon member sugars or saccharides (monomers), corresponding disaccharides (dimers), corresponding trisaccharides (trimers), corresponding tetrasaccharides (tetramers), and/or the like. Hexose includes glucose, glacatose, sucrose, fructose, allose, altrose, gulose, idose, mannose, sorbose, talose, tagatose, any other isomer of six carbon sugars, and/or the like. Desirably, at least a portion of hexose may be at least somewhat easily removable from the feedstock, such as by crushing, milling, pulverizing, washing, rinsing, diffusion processing, heating, adjusting pH, and/or the like. Easily removed hexose may also be referred to as free hexose. Hexose may include and/or form complexes of relatively simple sugars, such as a disaccharide including sucrose, lactose, and maltose and/or a trisaccharide. According to one embodiment, hexose refers to sugar not bound in polymer form. Polymer form refers to having many repeating units, such as in cellulose.

The step of removing hexose from the feedstock to form or leave a lignocellulosic material broadly refers to separating or removing at least a portion of the hexose or sometimes referred to as soluble sugars from the feedstock. Desirably, the sugars can be removed with mechanical and/or water washing processes, such as without breaking of chemical bonds or linkages. According to one embodiment, removing hexose from the feedstock excludes the use of a fungal process, a biological process, an algae process, an enzyme process, a free enzyme process, and/or the like.

Removing broadly refers to separating, taking away, eliminating, extracting, juicing, and/or the like, such as by crushing, milling, pulping, pulverizing, washing, rinsing, diffusion processing, heating, adjusting pH, and/or the like. Any suitable mechanical and/or process equipment may be used in the removing step, such as cutters, choppers, roller mills, kettles, diffusers, and/or the like.

Lignocellulosic material broadly refers to a feedstock remainder or portion with an at least somewhat reduced hexose content, such as less than about 50 percent of the hexose of the feedstock, less than about 70 percent of the hexose of the feedstock, less than about 80 percent of the hexose of the feedstock, less than about 90 percent of the hexose of the feedstock, less than about 95 percent of the hexose of the feedstock, and/or the like.

Lignocellulosic material may include lignin, hemicellulose, pectin, cellulose, starch, remaining soluble sugar and/or the like. Lignocellulosic material or lignocellulose may include tightly bound carbohydrate polymers, such as cellulose and hemicellulose combined with lignin by hydrogen bonding and/or covalent bonding, for example. The lignocellulosic material may include sugar cane bagasse, energy cane bagasse, rice straw, corn stover, wheat straw, maize stover, sorghum stover, sweet sorghum stover, cotton remnant, sugar beet pulp, any other suitable biomass material, and/or the like. According to one embodiment, all the lignocellulosic material of the process comes from the feedstock with the hexose removed or reduced. In the alternative, the lignocellulosic material may include additional or supplemental biomass from a suitable source, such as switchgrass, miscanthus, other grasses, softwood, hardwood, wood waste, sawdust, paper, paper waste, agricultural waste, municipal waste and/or the like.

Lignin broadly refers to a biopolymer that may be part of secondary cell walls in plants, such as a complex highly cross-linked aromatic polymer that covalently links to hemicellulose. Hemicellulose broadly refers to a branched sugar polymer composed mostly of pentoses, such as with a generally random amorphous structure and up to hundreds of thousands of pentose units. Cellulose broadly refers to an organic compound with the formula $(C_6H_{10}O_5)_z$, where z includes any suitable integer. Cellulose may include a polysaccharide with a linear chain of several hundred to over ten thousand hexose units and a high degree of crystalline structure, for example. Depolymerizing cellulose to hexose may include more severe and/or harsher conditions than depolymerizing hemicellulose, such as due to the crystalline structure of the cellulose.

Converting broadly refers to altering the physical and/or chemical nature and/or properties of an object or item, such as in manufacturing. Converting may also include changing from one form or function to another.

According to one embodiment, converting to butanol or biofuel includes the use of fermentation processes, such as using yeast, bacteria, cyanobacteria, algae, enzymes, and/or the like. Fermentation broadly refers to a chemical change, such as with effervescence or release of gas. Fermentation may include an enzyme controlled aerobic or anaerobic breakdown of an energy-rich compound, such as a carbohydrate to carbon dioxide and an alcohol and/or an organic acid. In the alternative, fermentation broadly refers to an enzyme controlled transformation of an organic compound. Enzymes broadly refer biologically derived molecules that can catalyze or facilitate chemical reactions or transformations. Either on their own or in conjunction with other molecules sometimes referred to as co-factors. Enzymes may include proteins, for example.

Suitable converting processes for butanol or biofuel may include naturally occurring hexose consumers and/or genetically modified hexose consumers. Naturally occurring organisms may produce alcohols or other oxygen containing compounds, such as may be used directly or may be converted to an ether and/or the like. Genetically modified organisms may directly produce a butanol product and/or a butanol derivative. In the alternative, genetically modified organisms may produce an intermediate compound.

Alcohol broadly refers to an organic compound in which a hydroxyl group (—OH) binds to a carbon atom of an alkyl or substituted alkyl group. Alcohols may include the general formula of $C_nH_{2n+1}OH$ where n includes any suitable integer, such as 1, 2, 3, 4, 5, 6, 7, 8, 9, 10, 20, 50, and/or the like. Alcohol, as defined in context of this specification, may include methanol, ethanol, propanol, butanol, hexanol, and/or the like. According to one embodiment, the process may produce one or more types of alcohol, such as in a combined fermentor and/or in individual fermentors.

The process may produce any suitable amount or combination of different alcohols, such as a methanol to ethanol ratio of at least 0.05 kilotons of methanol to 1.0 kiloton of ethanol, at least 0.1 kilotons of methanol to 1.0 kiloton of ethanol, at least 0.25 kilotons of methanol to 1.0 kiloton of ethanol, at least 0.5 kilotons of methanol to 1.0 kiloton of ethanol, at least 0.75 kilotons of methanol to 1.0 kiloton of ethanol, at least 1.0 kiloton of methanol to 1.0 kiloton of ethanol, and/or the like.

Depolymerizing broadly refers to taking something larger and breaking it into smaller units or pieces. Depolymerizing may include breaking or severing chemical bonds, such as to release monomers (1 unit) from a polymeric backbone or chain. Depolymerizing may also produce dimers (2 units), trimers (3 units), tetramers (4 units), any other suitable oligomers (few units), and/or the like, such as intermediates and/or compete products.

Depolymerizing may be done by any suitable mechanism, such as a hydrolysis process, an acidic process (pH 7 and below), a basic or alkali process (pH above 7), an enzymatic process, a solvent process, a thermo-mechanical process, and/or the like. Acid processes may include concentrated and/or dilute acid steps, such as with sulfuric acid, sulfurous acid, hydrochloric acid, phosphoric acid, organic acids, and/or the like. Basic processes may include caustic materials, such as ammonia, calcium hydroxide, calcium oxide, magnesium hydroxide sodium hydroxide, potassium hydroxide, sodium carbonate, potassium carbonate, sodium bicarbonate, potassium bicarbonate, and/or the like. One or more depolymerizing processes may be combined for a synergistic result.

Desirably, but not necessarily, the depolymerizing step results in a stream comprising primarily pentose, such as without a significant amount of hexose. The pentose content may be at least 70 percent of the total sugars from depolymerizing, at least 80 percent of the total sugars from depolymerizing, at least 85 percent of the total sugars from depolymerizing, at least 90 percent of the total sugars from depolymerizing, at least 95 percent of the total sugars from depolymerizing, at least 98 percent of the total sugars from depolymerizing, at least 99 percent of the total sugars from depolymerizing, about 100 percent of the total sugars from depolymerizing, and/or the like.

Pentose broadly refers to five (5) carbon member sugars or saccharides (monomers), corresponding disaccharides (dimers), corresponding trisaccharides (trimers), corresponding tetrasaccharides (tetramers), and/or the like. Pentose includes xylose, ribose, arabinose, ribulose, xylulose, lyxose, any other isomer of five carbon sugars, and/or the like. Desirably, at least a portion of pentose may be separated or derived from the hemicellulose. Pentose may include or form complexes of relatively simple sugars, such as a disaccharide and/or a trisaccharide. According to one embodiment, pentose refers to sugar bound in polymer form that can be liberated or separated, such as with mild to moderate processing to break down the hemicellulose into simpler segments or monosaccharide units.

The residue may include any suitable material, such as cellulose, lignin, remaining hemicellulose, remaining soluble sugar, pectin, ash, and/or the like. Desirably, but not necessarily, residue may be consumed or used for producing energy, such as in a powerhouse for generation of heat or steam used in the processes and/or electricity (steam and a turbine generator set), and/or the like. According to one embodiment, the residue can be used to produce energy including burning or combusting the residue in a fired heater or a boiler unit and generating steam. Desirably but not necessarily, the residue is dewatered and/or dried before combustion, such as to improve fuel value. In the alternative, the residue may be used for other purposes, such as compost, fertilizer, animal feed, landfill, and/or the like.

According to one embodiment, the reside may be treated to breakdown or depolymerize the cellulose to form hexose and a reduced residue. The reduced residue may include remaining cellulose, lignin, remaining hemicellulose, remaining soluble sugar, pectin, ash and/or the like. The hexose from the cellulose may be converted to butanol and/or biodiesel as described above with respect to the hexose initially removed form the feedstock. The hexose from the cellulose may be combined with the feedstock hexose in the same fermentor. In the alternative, the hexose from the cellulose may be consumed in a separate fermentor, such as to produce butanol and/or biodiesel.

Optionally, the hexose from the cellulose may be converted to biodiesel material, such as by the types and/or kinds of mechanisms or processes discussed above with respect to pentose conversion to biodiesel material. Desirably, but not necessarily, the hexose and the pentose streams remain separated, such as to not have competing reactions or competing food supplies in the converting processes or for the organisms. In the alternative, the hexose and pentose may be combined in a mixed fermentor with one or more biological processes to consume both sugars.

The residue or reduced residue may be dewatered and/or dried to improve fuel characteristics. The residue or reduced residue may be subjected to any other suitable pretreatment step, such as pH adjustment, mechanical processing, chemical processing, washing, liquid extraction, centrifugation and/or the like. The residue or reduced residue may be burned alone or may be consumed with supplemental fuel, such as coal or natural gas. The overall process and plant may be a net exporter or energy, such as selling electricity back to the electrical distribution grid. According to one embodiment, the residue provides adequate energy for the complex so that no external or supplemental fuel to meet the energy needs is consumed.

According to one embodiment, converting to a biodiesel material may include the use of fermentation processes, such as with yeast, bacteria, cyanobacteria, algae, enzyme, and/or the like. The converting the pentose to biodiesel material may include an algae process, a bacterial process, a fungal process, an enzyme process, a free enzyme process, and/or the like. These suitable converting processes may include naturally occurring pentose consumers and/or genetically modified pentose consumers. Naturally occurring organisms may produce fatty acids, such as may be esterified with an alcohol, hydrogenated with hydrogen, and/or the like to produce a biodiesel product. Genetically modified organisms may directly produce a biodiesel product. In the alternative, genetically modified organisms may produce a fatty acid.

Advantageously, the depolymerizing process may produce a relatively pure pentose stream as described above, such that pentose consumers do not preferentially consume hexose and reduce pentose conversion. The step of converting the pentose to biodiesel material may include a single cell organism and/or a microorganism process, such as may be easy to handle or process. In the alternative, the converting may include a multicell organism process.

Biodiesel material broadly refers to finished and/or intermediate compounds suitable for use as diesel fuel, kerosene fuel, heating fuel, aviation fuel, and/or the like. According to one embodiment, the biodiesel material may include polyunsaturated fatty acids, esters, fatty acid alkyl esters (FAAE) such as fatty acid methyl esters (FAME) or fatty acid ethyl esters (FAEE), triglycerides, alkanes, lipids, and/or the like. Desirably, but not necessarily, the biodiesel material may exclude materials derived from natural oil or essential oils, such as from plants like rapeseed, soy beans, and/or the like.

The integrated process of the invention may include any suitable ratio of butanol to biodiesel, such as a mass ratio of biodiesel to butanol of at least about 0.1 kilotons of biodiesel to 1.0 kiloton of butanol, at least about 0.2 kilotons of biodiesel to 1.0 kiloton of butanol, at least about 0.3 kilotons of biodiesel to 1.0 kiloton of butanol, at least about 0.35 kilotons of biodiesel to 1.0 kiloton of butanol, at least about 0.4 kilotons of biodiesel to 1.0 kiloton of butanol, at least about 0.45 kilotons of biodiesel to 1.0 kiloton of butanol, at least about 0.5 kilotons of biodiesel to 1.0 kiloton of butanol, at least about 0.55 kilotons of biodiesel to 1.0 kiloton of butanol, at least about 0.6 kilotons of biodiesel to 1.0 kiloton of butanol, at least about 0.7 kilotons of biodiesel to 1.0 kiloton of butanol, at least about 0.8 kilotons of biodiesel to 1.0 kiloton of butanol, at least about 0.9 kilotons of biodiesel to 1.0 kiloton of butanol, at least about 1.0 kiloton of biodiesel to 1.0 kiloton of butanol, and/or the like.

According to one embodiment, the process may also include the step of reacting the biodiesel material with an alcohol-based material to form a biodiesel product and glycerin, and optionally the step of converting the glycerin to additional biodiesel material. The ester reaction may include reacting a triglyceride with an alcohol-based material to form an ester and glycerin or glycerol. The alcohol-based material may include any suitable alcohol, such as methanol, ethanol, propanol, butanol, and/or the like. According to one embodiment, the alcohol-based material may include an alcohol derived from converting the hexose, as discussed and above and providing additional process integration. In the alternative, the biodiesel material may be hydrogenated to a hydrocarbon.

The biodiesel product may include any suitable material, such as fatty acid esters, other compounds within commercial or industrial diesel specifications, other compounds within aviation fuel specifications, other compounds within kerosene specifications, and/or the like. Biodiesel may include molecules having oxygen, such as for generally cleaner combustion. In the alternative, the biodiesel product may exclude oxygen containing molecules.

The step of converting the glycerin into additional biodiesel material may include returning the glycerin back to the step of converting the pentose to biodiesel. Optionally, the glycerin may be returned to the step of converting the hexose to butanol for producing additional butanol and/or alcohol, such as in the same or a separate fermentor as the hexose. In the alternative, the glycerin may be purified and sold as product glycerin, such as use in food, beverages, pharmaceuticals, cosmetics, munitions, polyurethanes, and/or the like.

According to one embodiment, the invention may include an integrated process of coproducing butanol and biodiesel. The process may include the step of removing hexose from sugarcane to form a lignocellulosic material, and the step of converting the hexose to ethanol or methanol. The process may include the step of depolymerizing the lignocellulosic material to form pentose and a residue, and the step of converting the pentose to a biodiesel material. The process may also include the step of consuming the residue to produce energy, and the step of reacting the biodiesel material with the methanol and/or other alcohol to form a biodiesel product and glycerin. The process may also include the step of converting the glycerin to additional biodiesel material. The process may produce a mass ratio of biodiesel to butanol of at least about 0.2 kilotons of biodiesel to 1.0 kiloton of butanol.

According to one embodiment, the invention may include an integrated butanol and biodiesel plant. The plant may include a hexose removal unit adapted for removing hexose from a feedstock to form a lignocellulosic material, and a hexose conversion unit adapted for converting hexose to butanol. The plant may also include a pentose depolymerization unit adapted for removing pentose from the lignocellulosic material to form a residue, and a pentose conversion unit adapted for converting pentose to a biodiesel material. Optionally, the plant may also include an energy conversion unit adapted for consuming the residue and producing energy.

Plant and/or production facility broadly refers to a collection of process equipment for performing a process, associated piping and/or conveyors, associated utilities, and/or the like, such as generally formed from one or more process blocks or units. Process blocks or units broadly refer to subparts or components of a plant, such as to accomplish or perform one or more specific tasks.

The integrated plant may further include an esterification unit adapted to react the biodiesel material with an alcohol-based material to form a biodiesel product and glycerin, and a line adapted for supplying the glycerin to the pentose conversion unit. Line broadly refers to any suitable transportation mechanism, such as a pipe, a pump, a gravity flow, a channel, a conduit, a duct, and/or the like.

According to one embodiment, the pentose removal or pentose depolymerization unit may use or employ an acidic process, a basic process, an enzymatic process, a solvent process, and/or the like. The pentose conversion unit may use or employ a single cell organism and/or a microorganism. The pentose conversion unit may use an algae process, a bacterial process, a fungal process, a free enzyme process and/or the like.

The integrated plant may produce any suitable mass ratio of biodiesel to butanol, such as at least about 0.2 kilotons of biodiesel to 1.0 kiloton of butanol, at least about 0.35 kilotons of biodiesel to 1.0 kiloton of butanol, at least about 0.55 kilotons of biodiesel to 1.0 kiloton of butanol, and/or the like.

Any embodiment described herein as a process may also be embodied as a plant or production facility of corresponding structure and/or function. Similarly, any embodiment described herein as a plant may also be embodied as a process or method of corresponding step and/or function.

According to one embodiment, the invention may include an integrated process of coproducing sugar product and biofuel. The process may include the step of removing hexose from a feedstock to form a lignocellulosic material, and the step of converting the hexose to a sugar product. The process may also include the step of depolymerizing the lignocellulosic material to form pentose and a residue, and the step of converting the pentose to butanol and/or biodiesel material.

Sugar product broadly refers to raw sugar, crystallized sugar, refined sugar, confectioners sugar, brown sugar, light brown sugar, dark brown sugar, fancy molasses, light molasses, dark molasses, cooking molasses, unsulphured molasses, sulphured molasses, blackstrap molasses, rum, light rum, dark rum, spiced rum, and/or the like. Sugar product broadly may include nutritional materials or food items for humans, livestock, and/or the like.

According to one embodiment, the invention may include an integrated process of coproducing biofuels. The process may include the step of removing hexose from a feedstock to form a lignocellulosic material, and the step of converting the hexose to butanol and/or a biodiesel material. The process may also include the step of depolymerizing the lignocellulosic material to form pentose and a residue, and the step of converting the pentose to butanol and/or a biodiesel material.

Any suitable combination of biofuel products are within the scope of this invention, such as hexose to butanol and pentose to butanol, hexose to butanol and pentose to biodiesel, hexose to biodiesel and pentose to biodiesel, hexose to biodiesel and pentose to butanol, hexose to sugar product and pentose to butanol, hexose to sugar product and pentose to biodiesel, and/or the like.

According to one embodiment, this invention may include one or more biofuels made by the any of the processes or plants described herein, such as a biofuels made by the integrated process including the step of removing hexose from a feedstock to form a lignocellulosic material, the step of converting the hexose to a butanol, the step of depolymerizing the lignocellulosic material to form pentose and a residue, and the step of converting the pentose to a biodiesel material.

According to one embodiment, this invention may include butanol made by any of the processes or plants described herein, such as 1-butanol, 2-butanol, iso-butanol, any other suitable isomer, any other suitable product of butanol, any other suitable derivative of butanol, and/or the like.

EXAMPLES

Comparative Example 1

A conventional sugar cane to ethanol fermentation plant produces 370 kilotons of ethanol product. FIG. 1 as discussed above, shows the basic components of the plant. Kilotons refer to thousands of metric tons where a metric ton is 1,000 kilograms. The plant consumes 4.8 megatons of sugar cane feedstock. Megatons refer to millions of metric tons. The crushing and milling of the sugar cane results in 720 kilotons of hexose sugar juice for the fermentor (based on 15% hexose content). The crushing and milling produces 4 megatons of bagasse (lignocellulosic material) which combusts to produce steam used in the crushing and milling and also in the hexose fermentation. The bagasse combustion also results in electricity used in the crushing and milling, also in the hexose fermentation, and 300 gigawatt hours for export to the electrical distribution grid. The hexose fermentation results in 370 kilotons of ethanol product (based on 51% ethanol yield on sugar). All numbers are based on annual production rates.

Example 1

An integrated biogasoline and biodiesel plant produces 370 kilotons of ethanol, according to one embodiment. FIG. 2 as discussed above, shows the basic components of the integrated plant. Optionally, the integrated plant produces 350 kilotons of ethanol and 25 kilotons of methanol, such as with two hexose fermentors utilizing different organisms or pathways for production of the respective alcohols.

The integrated plant consumes 4.8 megatons of sugar cane in the crushing and milling resulting in 720 kilotons of hexose sugar juice and 4 megatons of bagasse residue. The sugar juice ferments into the produced product alcohols. The lignin and cellulose residue combusts to produce steam and electricity for use in the process or export to the electrical distribution grid. The pentose sugar juice ferments to produce the biodiesel material and/or oil. The pentose fermentation in a pentose fermentor utilizes different organisms or pathways from the hexose fermentation.

Example 2

An integrated biogasoline and biodiesel plant of Example 1 further includes an esterification unit, according to one embodiment. FIG. 3 as discussed above, shows the basic components of the integrated plant with an esterification unit.

The esterification unit converts the biodiesel material and an alcohol to biodiesel product and glycerin. The biodiesel product includes fatty acid esters. Depending on the alcohol used different esters result, such as methyl esters from methanol, ethyl esters from ethanol, and/or propyl esters from propanol. Optionally, the alcohol comes from the hexose fermentor. In the alternative, the alcohol comes from off-site production.

As used herein the terms "having", "comprising", and "including" are open and inclusive expressions. Alternately, the term "consisting" is a closed and exclusive expression. Should any ambiguity exist in construing any term in the claims or the specification, the intent of the drafter is toward open and inclusive expressions.

Regarding an order, number, sequence and/or limit of repetition for steps in a method or process, the drafter intends no implied order, number, sequence and/or limit of repetition for the steps to the scope of the invention, unless explicitly provided.

It will be apparent to those skilled in the art that various modifications and variations can be made in the disclosed structures and methods without departing from the scope or spirit of the invention. Particularly, descriptions of any one embodiment can be freely combined with descriptions or other embodiments to result in combinations and/or variations of two or more elements or limitations. Other embodiments of the invention will be apparent to those skilled in the art from consideration of the specification and practice of the invention disclosed herein. It is intended that the specification and examples be considered exemplary only, with a true scope and spirit of the invention being indicated by the following claims.

What is claimed is:

1. An integrated process of coproducing butanol and biodiesel, the process comprising:
    removing hexose from a feedstock to form a lignocellulosic material;
    converting the hexose to butanol;
    depolymerizing the lignocellulosic material to form pentose and a residue; and
    converting the pentose to a biodiesel material.

2. The process of claim 1, further comprising a mass ratio of biodiesel to butanol of at least about 0.2 kilotons of biodiesel to 1.0 kiloton of butanol.

3. The process of claim 1, wherein the feedstock comprises sugarcane, energy cane, corn, maize, sorghum, sweet sorghum, sugar beet, or combinations thereof.

4. The process of claim 1, wherein the depolymerizing the lignocellulosic material to form pentose comprises an acidic process, a basic process, an enzymatic process, a solvent process, or combinations thereof.

5. The process of claim 1, wherein the converting the pentose to the biodiesel material comprises a microorganism process.

6. The process of claim 1, wherein the converting the pentose to the biodiesel material comprises an algae process, a bacterial process, a fungal process, a free enzyme process, or combinations thereof.

7. The process of claim 1, wherein the removing hexose from the feedstock comprises crushing, milling, or diffusion.

8. The process of claim 1, wherein the converting the hexose to the butanol comprises butanol fermentation.

9. The process of claim 1, further comprising consuming the residue to produce energy comprising:
    burning the residue in a fired heater or a boiler unit; and
    generating steam.

10. The process of claim 1, wherein the lignocellulosic material comprises bagasse, rice straw, corn stover, miscanthus, switchgrass, wheat straw, wood, wood waste, paper, paper waste, agricultural waste, municipal waste, or combinations thereof.

11. The process of claim 1, wherein the residue comprises cellulose or lignin.

12. The process of claim 1, wherein the biodiesel material comprises polyunsaturated fatty acids, esters, triglycerides, alkanes, or combinations thereof.

13. The process of claim 1, wherein:
    the hexose comprises glucose, sucrose, or fructose; and
    the pentose comprises xylose.

14. The process of claim 1, further comprising:
    reacting the biodiesel material with an alcohol-based material to form a biodiesel product and glycerin; and
    optionally converting the glycerin to additional biodiesel material.

15. The process of claim 14, wherein the alcohol-based material comprises ethanol or methanol.

16. The process of claim 14, wherein the alcohol-based material comprises the butanol derived from converting hexose.

17. One or more biofuels made by the process of claim 1.

18. An integrated process of coproducing butanol and biodiesel, the process comprising:
    removing hexose from sugarcane to form a lignocellulosic material;
    converting the hexose to butanol;
    depolymerizing the lignocellulosic material to form pentose and a residue;
    converting the pentose to a biodiesel material;
    consuming the residue to produce energy;
    reacting the biodiesel material with methanol to form a biodiesel product and glycerin; and
    converting the glycerin to additional biodiesel material;
    wherein the process produces a mass ratio of biodiesel to butanol of at least about 0.2 kilotons of biodiesel to 1.0 kiloton of butanol.

19. An integrated butanol and biodiesel plant, the plant comprising:
    a hexose removal unit adapted for removing hexose from a feedstock to form a lignocellulosic material;
    a hexose conversion unit adapted for converting hexose to butanol;
    a pentose depolymerization unit adapted for removing pentose from the lignocellulosic material to form a residue; and
    a pentose conversion unit adapted for converting pentose to a biodiesel material.

20. The plant of claim 19, further comprising:
    an esterification unit adapted to react the biodiesel material with an alcohol-based material to form a biodiesel product and glycerin; and
    a line adapted for supplying the glycerin to the pentose conversion unit.

21. The plant of claim 19, wherein the pentose depolymerization unit uses an acidic process, a basic process, an enzymatic process, a solvent process, or combinations thereof.

22. The plant of claim 19, wherein the pentose conversion unit uses a microorganism.

23. The plant of claim 19, wherein the pentose conversion unit uses an algae process, a bacterial process, a fungal process, a free enzyme process, or combinations thereof.

24. The plant of claim 19, further comprising a mass ratio of biodiesel to butanol of at least about 0.2 kilotons of biodiesel to 1.0 kiloton of butanol.

25. An integrated process of coproducing biofuels, the process comprising:
- removing hexose from a feedstock and to form a lignocellulosic material;
- converting the hexose to butanol or a biodiesel material;
- depolymerizing the lignocellulosic material to form pentose and a residue; and
- converting the pentose to butanol or a biodiesel material.

* * * * *